United States Patent
Singh et al.

(10) Patent No.: US 7,524,805 B2
(45) Date of Patent: Apr. 28, 2009

(54) AZEOTROPE-LIKE COMPOSITIONS OF TETRAFLUOROPROPENE AND HYDROFLUOROCARBONS

(75) Inventors: Rajiv R. Singh, Getzville, NY (US); Hang T. Pham, Amherst, NY (US); Gary M. Knopeck, Lakeview, NY (US); Louis E. Herena, Scarsdale, NY (US); Jeremy N. Diringer, Morristown, NJ (US)

(73) Assignee: Honeywell International Inc., Morristown, NJ (US)

( * ) Notice: Subject to any disclaimer, the term of this patent is extended or adjusted under 35 U.S.C. 154(b) by 270 days.

(21) Appl. No.: 10/837,526

(22) Filed: Apr. 29, 2004

(65) Prior Publication Data

US 2005/0245421 A1 Nov. 3, 2005

(51) Int. Cl.
*C11D 17/00* (2006.01)
(52) U.S. Cl. ........................... 510/408; 510/412
(58) Field of Classification Search ................. 510/408, 510/412
See application file for complete search history.

(56) References Cited

U.S. PATENT DOCUMENTS

| | | | |
|---|---|---|---|
| 2,931,840 A | 4/1960 | Marquis | 260/653.3 |
| 2,970,988 A | 2/1961 | Lo | 260/87.7 |
| 3,085,918 A | 4/1963 | Sherliker | 134/30 |
| 3,723,318 A | 3/1973 | Butler | |
| 3,884,828 A | 5/1975 | Butler | |
| 4,788,352 A | 11/1988 | Smutny | 570/153 |
| 5,182,040 A | 1/1993 | Bartlett | 252/67 |
| 5,387,357 A * | 2/1995 | Shiflett et al. | 252/67 |
| 5,648,017 A | 7/1997 | Bartlett | 252/67 |
| 5,714,083 A | 2/1998 | Turner | |
| 5,811,603 A | 9/1998 | Elsheikh | 570/166 |
| 5,968,406 A * | 10/1999 | Bartlett et al. | 252/67 |
| 6,025,532 A | 2/2000 | Sage | 570/171 |
| 6,111,150 A | 8/2000 | Sakyu et al. | |
| 6,235,951 B1 | 5/2001 | Sakyu et al. | 570/156 |
| 6,316,681 B1 | 11/2001 | Yoshikawa et al. | 570/166 |
| 6,516,837 B2 | 2/2003 | Thomas et al. | 141/67 |
| 6,589,355 B1 | 7/2003 | Thomas et al. | 134/3 |
| 2004/0089839 A1 * | 5/2004 | Thomas et al. | 252/67 |
| 2004/0119047 A1 * | 6/2004 | Singh et al. | 252/71 |
| 2004/0127383 A1 * | 7/2004 | Pham et al. | 510/412 |

FOREIGN PATENT DOCUMENTS

| | | |
|---|---|---|
| EP | 0 398 147 | 11/1990 |
| JP | 63211245 | 2/1988 |
| JP | 63303950 | 12/1988 |
| JP | 04 110388 | 4/1992 |

OTHER PUBLICATIONS

U.S. Appl. No. 10/694,272, filed Oct. 27, 2003; Process for Producing Fluoropropenes; Merkel et al.
U.S. Appl. No. 10/694,273, filed Oct. 27, 2003; Compositions Containing Fluorine Substituted Olefins; Singh et al.
U.S. Appl. No. 10/695,212, filed Oct. 27, 2003; Fluorinated Alkene Refrigerant Compositions; Thomas et al.
The Journal of the American Chemical Society vol. LXXVII; Apr.-Jun. 1955; Noyes, W. Albert, Jr., Editor; Easton, PA; pp. 3149-3151.
Polyurethanes Chemistry and Technology vol. XVI, Part II. Technology; 1964; Saunders & Frisch; New York, NY; pp. 193-225.

* cited by examiner

*Primary Examiner*—Gregory E Webb
(74) *Attorney, Agent, or Firm*—Colleen D. Szuch

(57) ABSTRACT

Provided are azeotrope-like compositions comprising tetrafluoropropene and hydrofluorocarbons and uses thereof, including use in refrigerant compositions, refrigeration systems, blowing agent compositions, and aerosol propellants.

32 Claims, No Drawings

AZEOTROPE-LIKE COMPOSITIONS OF TETRAFLUOROPROPENE AND HYDROFLUOROCARBONS

CROSS REFERENCE TO RELATED APPLICATIONS

The present application is also related to and incorporates by reference each of the following pending U.S. patent applications: U.S. application Ser. Nos. 10/694,273, filed Oct. 27, 2003; 10/695,212, filed Oct. 27, 2003; and 10/694,272 filed 10/27/2003.

The present application is related to and claims the priority benefit of the following U.S. Provisional Applications, each of which is filed concurrently herewith and incorporated herein by reference: 60/567,427, 60/567,425, 60/567,428, 60/567,427, and 60/567,429, each entitled "Processes for Synthesis of 1,3,3,3-tetrafluoropropene."

The present application is related to and claims the priority benefit of the following regular U.S. Applications, each of which is filed concurrently herewith and incorporated herein by reference: U.S. Ser. Nos. 10/837,521, entitled "Heat Transfer Fluid Comprising Trans-1,3,3,3-tetrafluoropropene," and U.S. Ser. No. 10/837,525, entitled "Compositions Containing Fluorine Substituted Olefins."

FIELD OF INVENTION

The present invention relates generally to compositions comprising 1,3,3,3-tetrafluoropropene. More specifically, the present invention provides azeotrope-like compositions of 1,1,1,3-tetrafluoropropene and uses thereof.

BACKGROUND

Fluorocarbon based fluids have found widespread use in industry in a number of applications, including as refrigerants, aerosol propellants, blowing agents, heat transfer media, and gaseous dielectrics. Because of the suspected environmental problems associated with the use of some of these fluids, including the relatively high global warming potentials associated therewith, it is desirable to use fluids having low or even zero ozone depletion potential, such as hydrofluorocarbons ("HFCs"). Thus, the use of fluids that do not contain chlorofluorocarbons ("CFCs") or hydrochlorofluorocarbons ("HCFCs") is desirable. Additionally, the use of single component fluids or azeotropic mixtures, which do not fractionate on boiling and evaporation, is desirable. However, the identification of new, environmentally-safe, non-fractionating mixtures is complicated due to the fact that azeotrope formation is not readily predictable.

The industry is continually seeking new fluorocarbon based mixtures that offer alternatives, and are considered environmentally safer substitutes for CFCs and HCFCs. Of particular interest are mixtures containing both hydrofluorocarbons and other fluorinated compounds, both of low ozone depletion potentials. Such mixtures are the subject of this invention.

DESCRIPTION OF PREFERRED EMBODIMENTS

The present inventors have developed several compositions that help to satisfy the continuing need for alternatives to CFCs and HCFCs. According to certain embodiments, the present invention provides azeotrope-like compositions comprising, or consisting essentially of, 1,1,1,3-tetrafluoropropene ("HFO-1234ze"), preferably trans-1,1,1,3-tetrafluoropropene ("transHFO-1234ze") and a component selected from the group consisting of 1,1-difluoroethane ("HFC-152a"), 1,1,1,2,3,3,3-heptafluoropropane ("HFC-227ea"), 1,1,1,2, -tetraafluoethane ("HFC-134a"), 1,1,1,2,2-pentafluoroethane ("HFC-125") and combinations of two or more of these. Thus, the present invention overcomes the aforementioned shortcomings by providing azeotrope-like compositions that are substantially free of CFCs and HCFCs and which exhibit relatively constant boiling point and vapor pressure characteristics.

The preferred compositions of the invention tend to exhibit relatively low global warming potentials ("GWPs"). Accordingly, applicants have recognized that such compositions can be used to great advantage in a number of applications, including as replacements for CFCs, HCFCs, and HFCs (such as HFC-134a) in refrigerant, aerosol, and other applications.

Additionally, applicants have recognized surprisingly that the azeotrope-like compositions of the present invention exist and can be readily formed in view of the teachings contained herein. Accordingly, one aspect of the present invention provides methods of producing azeotrope-like compositions comprising the step of combining HFO-1234, preferably HFO-1234ze, and even more preferably transHFO-1234ze, and a compound selected from the group consisting of 1,1-difluoroethane ("HFC-152a"), 1,1,1,2,3,3,3-heptafluoropropane ("HFC-227ea"), 1,1,1,2, -tetraafluoethane ("HFC-134a"), 1,1,1,2,2-pentafluoroethane ("HFC-125") and combinations of two or more of these, in amounts effective to produce an azeotrope-like composition.

In addition, applicants have recognized that the azeotrope-like compositions of the present invention exhibits properties that make that make them advantageous for use as, or in, refrigerant compositions. Accordingly, yet other aspects of the present invention provide refrigerant compositions comprising one or more azeotrope-like compositions of the present invention.

In another embodiment, the compositions of this invention may be used as propellants in sprayable compositions, either alone or in combination with known propellants. The propellant composition comprises, more preferably consists essentially of, and, even more preferably, consists of the compositions of the invention. The active ingredient to be sprayed together with inert ingredients, solvents, and other materials may also be present in the sprayable mixture. Preferably, the sprayable composition is an aerosol. Suitable active materials to be sprayed include, without limitation, cosmetic materials such as deodorants, perfumes, hair sprays, cleansers, and polishing agents as well as medicinal materials such as anti-asthma and anti-halitosis medications.

The present compositions find particular advantage in methods and systems involving aerosol compositions, particularly in medicinal compositions, cleaning composition, and other sprayable compositions. Those of skill in the art will be readily able to adapt the present compositions for use in such applications without undue experimentation.

Azeotrope-Like Compositions

As used herein, the term "azeotrope-like" is intended in its broad sense to include both compositions that are strictly azeotropic and compositions that behave like azeotropic mixtures. From fundamental principles, the thermodynamic state of a fluid is defined by pressure, temperature, liquid composition, and vapor composition. An azeotropic mixture is a system of two or more components in which the liquid composition and vapor composition are equal at the stated pressure and temperature. In practice, this means that the components of an azeotropic mixture are constant-boiling and cannot be separated during a phase change.

Azeotrope-like compositions are constant boiling or essentially constant boiling. In other words, for azeotrope-like compositions, the composition of the vapor formed during boiling or evaporation is identical, or substantially identical, to the original liquid composition. Thus, with boiling or evaporation, the liquid composition changes, if at all, only to a minimal or negligible extent. This is to be contrasted with non-azeotrope-like compositions in which, during boiling or evaporation, the liquid composition changes to a substantial degree. All azeotrope-like compositions of the invention within the indicated ranges as well as certain compositions outside these ranges are azeotrope-like.

The azeotrope-like compositions of the invention may include additional components that do not form new azeotrope-like systems, or additional components that are not in the first distillation cut. The first distillation cut is the first cut taken after the distillation column displays steady state operation under total reflux conditions. One way to determine whether the addition of a component forms a new azeotrope-like system so as to be outside of this invention is to distill a sample of the composition with the component under conditions that would be expected to separate a non-azeotropic mixture into its separate components. If the mixture containing the additional component is non-azeotrope-like, the additional component will fractionate from the azeotrope-like components. If the mixture is azeotrope-like, some finite amount of a first distillation cut will be obtained that contains all of the mixture components that is constant boiling or behaves as a single substance.

It follows from this that another characteristic of azeotrope-like compositions is that there is a range of compositions containing the same components in varying proportions that are azeotrope-like or constant boiling. All such compositions are intended to be covered by the terms "azeotrope-like" and "constant boiling". As an example, it is well known that at differing pressures, the composition of a given azeotrope will vary at least slightly, as does the boiling point of the composition. Thus, an azeotrope of A and B represents a unique type of relationship, but with a variable composition depending on temperature and/or pressure. It follows that, for azeotrope-like compositions, there is a range of compositions containing the same components in varying proportions that are azeotrope-like. All such compositions are intended to be covered by the term azeotrope-like as used herein.

It is well-recognized in the art that it is not possible to predict the formation of azeotropes. (See, for example, U.S. Pat. No. 5,648,017 (column 3, lines 64-65) and U.S. Pat. No. 5,182,040 (column 3, lines 62-63), both of which are incorporated herein by reference). Applicants have discovered unexpectedly that HFO-1234 and HFCs form azeotrope-like compositions.

According to certain preferred embodiments, the azeotrope-like compositions of the present invention comprise, and preferably consist essentially of, effective amounts of HFO-1234 and HFCs. The term "effective amounts" as used herein refers to the amount of each component which upon combination with the other component, results in the formation of an azeotrope-like composition of the present invention. The azeotrope-like compositions of the present invention can be produced by combining effective amounts of HFO-1234 and a component, preferably in fluid form, selected from the group consisting of 1,1-difluoroethane ("HFC-152a"), 1,1,1,2,3,3,3-heptafluoropropane ("HFC-227ea"), 1,1,1,2, -tetrafluroethane ("HFC-134a"), 1,1,1,2,2-pentafluoroethane ("HFC-125") and combinations of two or more of these. Any of a wide variety of methods known in the art for combining two or more components to form a composition can be adapted for use in the present methods to produce an azeotrope-like composition. For example, transHFO-1234ze and HFC-152a can be mixed, blended, or otherwise contacted by hand and/or by machine, as part of a batch or continuous reaction and/or process, or via combinations of two or more such steps. In light of the disclosure herein, those of skill in the art will be readily able to prepare azeotrope-like compositions according to the present invention without undue experimentation.

Preferably, such azeotrope-like compositions comprise, preferably consist essentially of, from greater than zero to about 99 wt. % of transHFO-1234ze and from about 1 wt. % to less than 100 wt. % of one or more components selected from the group consisting 1,1-difluoroethane ("HFC-152a"), 1,1,1,2,3,3,3-heptafluoropropane ("HFC-227ea"), 1,1,1,2, -tetrafluroethane ("HFC-134a"), and 1,1,1,2,2-pentafluoroethane ("HFC-125"). It will be appreciated by those skilled in the art that the production transHFO-1234ze will commonly result in product which includes a small proportion of compound which are not transHFO-1234ze. For example, it would be common in expected for a product designated as transHFO-1234ze to include a minor percentage, for example about 0.5 wt. % up to about 1 wt. % of other components, including particularly cisHFO-1234ze. The term "consisting essentially of transHFO-1234ze" used herein is intended to generally include such compositions.

More preferably, the present azeotrope-like compositions comprise, and preferably consist essentially of, from about 5 wt. % to about 90 wt. % of transHFO-1234ze and from about 10 wt. % to about 90 wt. % of one or more components selected from the group consisting 1,1-difluoroethane ("HFC-152a"), 1,1,1,2,3,3,3-heptafluoropropane ("HFC-227ea"), 1,1,1,2, -tetrafluroethane ("HFC-134a"), and 1,1,1,2,2-pentafluoroethane ("HFC-125"). Other preferred compositions comprise, or consist essentially of, greater than zero to about 60 wt. % of transHFO-1234ze and from about 40 wt. % to less than 100 wt. % of one or more components selected from the group consisting 1,1-difluoroethane ("HFC-152a"), 1,1,1,2,3,3,3-heptafluoropropane ("HFC-227ea"), 1,1,1,2, -tetrafluroethane ("HFC-134a"), and 1,1,1,2,2-pentafluoroethane ("HFC-125"). Unless otherwise indicated, all weight percents reported herein are based on the total weight of the HFO-1234 and the one or more components selected from the indicated group in the azeotrope-like composition.

According to certain preferred embodiments, the present transHFO-1234ze azeotrope-like compositions have a boiling point of from about −15° C. to about −50° C., and even more preferably from about −28° C. to about −50° C., at about 14 psia. In certain preferred embodiments, the present compositions have a boiling point of about −23° C.±2° C. In other preferred embodiments, the present compositions have a boiling point of about −18° C.±1° C. Additionally, in other preferred embodiments the present compositions have a boiling point of about −47° C.±2° C. Preferably, the HFO-1234 containing compositions of the present invention are substantially homogenous azeotrope-like compositions.

HFO-1234/HFC-134a

Certain preferred embodiments of the present invention provide azeotrope-like compositions comprising transHFO-1234ze and HFC-134a. Preferably, the novel azeotrope-like compositions of the present invention comprise effective amounts of transHFO-1234ze and HFO-134a. These embodiments preferably provide azeotrope-like compositions comprising, and preferably consisting essentially of, from greater than zero to about 75 weight percent transHFO-1234ze and from about 25 wt. % to less than 100 wt. % HFC-134a, more preferably from greater than zero to about 60 wt. % transHFO-1234ze and from about 40 wt. % to less than 100 wt. % HFO-134a, and even more preferably from about 1% to about 40 weight percent transHFO-1234ze and from about 60 wt. % to about 99 wt. % HFC-134a. In certain preferred embodiments, the azeotrope-like compositions comprise, and preferably consist essentially of, from about 5 wt. % to about 35 wt % transHFO-1234ze and from about 65 wt. % to about 95 wt. % HFO-134a.

Preferably, the HFO-1234/HFC-134a compositions of the present invention have a boiling of from about −26° C. to about −23° C. at about 14 psia.

Preferably, the HFO-1234/HFO-134a compositions of the present invention have a boiling of about −25° C.±3° C. at about 14 psia. In certain embodiments, the compositions have a boiling point of preferably about −25° C.±2° C., and even more preferably −25° C.±1° C., all measured at about 14 psia.

Preferably the HFO-1234 of these embodiments is transHFO-1234ze.

HFO-1234/HFC-125

In certain other preferred embodiments, the present invention provides azeotrope-like compositions comprising transHFO-1234ze and HFC-125. Preferably, such novel azeotrope-like compositions of the present invention comprise, or consist essentially of, effective amounts of transHFO-1234ze and HFC-125. These embodiments preferably provide azeotrope-like compositions comprising, and preferably consisting essentially of, from greater than zero to about 99 weight percent transHFO-1234ze and from about 1 wt. % to less than 100 wt. % HFC-125, more preferably from greater than zero to about 75 wt. % transHFO-1234ze and from about 25 wt. % to less than 100 wt. % HFC-125, even more preferably from about greater than zero to about 60 wt. % tansHFO-1234ze and from about 40 to less than 100 wt. % HFC-125, and even more preferably from about 1% to about 40 weight percent transHFO-1234ze and from about 60 wt. % to about 99 wt. % HFC-125. In certain preferred embodiments, the azeotrope-like compositions comprise, and preferably consist essentially of, from about 2 wt. % to about 15 wt % transHFO-1234ze and from about 85 wt. % to about 98 wt. % HFC-125.

Other preferred compositions comprise, or consist essentially of, from greater than zero to about 45 wt. % transHFO-1234ze and from about 55 to less than 100 wt. % HFC-125.

Preferably, the HFO-1234/HFC-125 compositions of the present invention have a boiling of about −44° C. to about −50° C., at about 14 psia.

Preferably the HFO-1234/HFC-125 compositions of the present invention have a boiling of about −47° C.±2° C., preferably −47° C±1° C. at about 14 psia.

HFO-1234/HFC-152a

In certain other preferred embodiments, the present invention provides azeotrope-like compositions comprising transHFO-1234ze and HFC-152a. Preferably, such novel azeotrope-like compositions of the present invention comprise, or consist essentially of, effective amounts of transHFO-1234ze and HFC-152a. These embodiments preferably provide azeotrope-like compositions comprising, and preferably consisting essentially of, from greater than zero to about 99 weight percent transHFO-1234ze and from about 1 wt. % to less than 100 wt. % HFC-152a, more preferably from greater than zero to about 50 wt. % transHFO-1234ze and from about 50 wt. % to less than 100 wt. % HFC-152a, and even more preferably from about greater than zero to about 40 wt. % transHFO-1234ze and from about 60% to less than 100 wt. % HFC-227ea. In certan preferred embodiments, the azeotrope-like compositions comprise, and preferably consist essentially of, from about 15 wt. % to about 30 wt % transHFO-1234ze and from about 70 wt. % to about 85 wt. % HFO-152a.

Preferably, the HFO-1234/HFC-152a compositions of the present invention have a boiling of about −17° C. to about −19° C., at about 14 psia.

Preferably, the HFO-1234/HFC-152a compositions of the present invention have a boiling of from about −22° C. to about −24° C. at about 14 psia.

Preferably, the HFO-1234/HFO-134a compositions of the present invention have a boiling of about −23° C.±2° C. at about 14 psia. In certain embodiments, the compositions have a boiling point of preferably about −23° C.±1° C. measured at about 14 psia.

Preferably the HFO-1234 of these embodiments is transHFO-1234ze.

HFO-1234/HFC-227ea

Certain preferred embodiments of the present invention provide azeotrope-like compositions comprising transHFO-1234ze and HFC-227ea. Preferably, the novel azeotrope-like compositions of the present invention comprise effective amounts of transHFO-1234ze and HFO-227ea. These embodiments preferably provide azeotrope-like compositions comprising, and preferably consisting essentially of, from greater than zero to about 75 weight percent HFC-227ea and from about 25 wt. % to less than 100 wt. % transHFO-1234ze, more preferably from greater than zero to about 60 wt. % HFC-227ea and from about 40 wt. % to less than 100 wt. % transHFC-1234ze, and even more preferably from about 1% to about 40 weight percent HFC-227ea and from about 60 wt. % to about 99 wt. % transHFO-1234ze. In certain preferred embodiments, the azeotrope-like compositions comprise, and preferably consist essentially of, from about 5 wt. % to about 35 wt % HFC-227ea and from about 65 wt. % to about 95 wt. % transHFO-1234ze.

Preferably, the HFO-1234/HFC-227ea compositions of the present invention have a boiling of from about −17° C. to about −19° C. at about 14 psia.

Preferably, the HFO-1234/HFO-227ea compositions of the present invention have a boiling of about −18° C.±2° C. at about 14 psia, and even more preferably about −18° C.±1° C., measured at about 14 psia.

Preferably the HFO-1234 of these embodiments is transHFO-1234ze.

Uses of the Compositions

The present compositions have utility in a wide range of applications. For example, one embodiment of the present invention relates to refrigerant compositions comprising the present azeotrope-like compositions.

The refrigerant compositions of the present invention may be used in any of a wide variety of refrigeration systems including air-conditioning, refrigeration, heat-pump systems, and the like. In certain preferred embodiments, the compositions of the present invention are used in refrigeration systems originally designed for use with an HFC-refrigerant, such as, for example, HFC-134a. The preferred compositions of the present invention tend to exhibit many of the desirable characteristics of HFC-134a and other HFC-refrigerants, including non-flammability, and a GWP that is as low, or lower than that of conventional HFC-refrigerants. In addition, the relatively constant boiling nature of the compositions of the present invention makes them even more desirable than certain conventional HFCs for use as refrigerants in many applications.

In certain other preferred embodiments, the present compositions are used in refrigeration systems originally designed for use with a CFC-refrigerant. Preferred refrigeration compositions of the present invention may be used in refrigeration systems containing a lubricant used conventionally with CFC-refrigerants, such as mineral oils, silicone oils, and the like, or may be used with other lubricants traditionally used with HFC refrigerants.

In certain embodiments, the compositions of the present invention may be used to retrofit refrigeration systems containing HFC, HCFC, and/or CFC-refrigerants and lubricants used conventionally therewith. Preferably, the present methods involve recharging a refrigerant system that contains a refrigerant to be replaced and a lubricant comprising the steps of (a) removing the refrigerant to be replaced from the refrigeration system while retaining a substantial portion of the lubricant in said system; and (b) introducing to the system a composition of the present invention. As used herein, the term "substantial portion" refers generally to a quantity of lubricant which is at least about 50% (by weight) of the quantity of lubricant contained in the refrigeration system prior to removal of the chlorine-containing refrigerant. Preferably, the substantial portion of lubricant in the system according to the present invention is a quantity of at least about 60% of the lubricant contained originally in the refrigeration system, and more preferably a quantity of at least about 70%. As used herein the term "refrigeration system" refers generally to any system or apparatus, or any part or portion of such a system or apparatus, which employs a refrigerant to provide cooling. Such refrigeration systems include, for example, air conditioners, electric refrigerators, chillers, transport refrigeration systems, commercial refrigeration systems and the like.

Any of a wide range of known methods can be used to remove refrigerants to be replaced from a refrigeration system while removing less than a major portion of the lubricant contained in the system. For example, because refrigerants are quite volatile relative to traditional hydrocarbon-based lubricants (the boiling points of refrigerants are generally less than 10° C. whereas the boiling points of mineral oils are generally more than 200° C.), in embodiments wherein the lubricant is a hydrocarbon-based lubricant, the removal step may readily be performed by pumping chlorine-containing refrigerants in the gaseous state out of a refrigeration system containing liquid state lubricants. Such removal can be achieved in any of a number of ways known in the art, including, the use of a refrigerant recovery system, such as the recovery system manufactured by Robinair of Ohio. Alternatively, a cooled, evacuated refrigerant container can be attached to the low pressure side of a refrigeration system such that the gaseous refrigerant is drawn into the evacuated container and removed. Moreover, a compressor may be attached to a refrigeration system to pump the refrigerant from the system to an evacuated container. In light of the above disclosure, those of ordinary skill in the art will be readily able to remove chlorine-containing lubricants from refrigeration systems and to provide a refrigeration system having therein a hydrocarbon-based lubricant and substantially no chlorine-containing refrigerant according to the present invention.

Any of a wide range of methods for introducing the present refrigerant compositions to a refrigeration system can be used in the present invention. For example, one method comprises attaching a refrigerant container to the low-pressure side of a refrigeration system and turning on the refrigeration system compressor to pull the refrigerant into the system. In such embodiments, the refrigerant container may be placed on a scale such that the amount of refrigerant composition entering the system can be monitored. When a desired amount of refrigerant composition has been introduced into the system, charging is stopped. Alternatively, a wide range of charging tools, known to those of skill in the art, is commercially available. Accordingly, in light of the above disclosure, those of skill in the art will be readily able to introduce the refrigerant compositions of the present invention into refrigeration systems according to the present invention without undue experimentation.

According to certain other embodiments, the present invention provides refrigeration systems comprising a refrigerant of the present invention and methods of producing heating or cooling by condensing and/or evaporating a composition of the present invention. In certain preferred embodiments, the methods for cooling an article according to the present invention comprise condensing a refrigerant composition comprising an azeotrope-like composition of the present invention and thereafter evaporating said refrigerant composition in the vicinity of the article to be cooled. Certain preferred methods for heating an article comprise condensing a refrigerant composition comprising an azeotrope-like composition of the present invention in the vicinity of the article to be heated and thereafter evaporating said refrigerant composition. In light of the disclosure herein, those of skill in the art will be readily able to heat and cool articles according to the present inventions without undue experimentation.

In another embodiment, the azeotrope-like compositions of this invention may be used as propellants in sprayable compositions, either alone or in combination with known propellants. The propellant composition comprises, more preferably consists essentially of, and, even more preferably, consists of the azeotrope-like compositions of the invention. The active ingredient to be sprayed together with inert ingredients, solvents, and other materials may also be present in the sprayable mixture. Preferably, the sprayable composition is an aerosol. Suitable active materials to be sprayed include, without limitation, cosmetic materials such as deodorants, perfumes, hair sprays, cleansers, and polishing agents as well as medicinal materials such as anti-asthma and anti-halitosis medications.

Yet another embodiment of the present invention relates to a blowing agent comprising one or more azeotrope-like compositions of the invention. In other embodiments, the invention provides foamable compositions, and preferably polyurethane and polyisocyanurate foam compositions, and methods of preparing foams. In such foam embodiments, one or more of the present azeotrope-like compositions are included as a blowing agent in a foamable composition, which composition preferably includes one or more additional components capable of reacting and foaming under the proper conditions to form a foam or cellular structure, as is well known in the art. Any of the methods well known in the art, such as those described in "Polyurethanes Chemistry and Technology," Volumes I and II, Saunders and Frisch, 1962, John Wiley and Sons, New York, N.Y., which is incorporated herein by reference, may be used or adapted for use in accordance with the foam embodiments of the present invention.

Other uses of the present azeotrope-like compositions include use as solvents, cleaning agents, and the like. Those of skill in the art will be readily able to adapt the present compositions for use in such applications without undue experimentation.

EXAMPLES

The invention is further illustrated in the following example which is intended to be illustrative, but not limiting in any manner. For examples 1-4, a ebulliometer of the general type described by Swietolslowski in his book "Ebulliometric Measurements" (Reinhold, 1945) was used.

Example 1

An ebulliometer consisting of vacuum jacketed tube with a condenser on top which is further equipped with a Quartz Thermometer is used. About 21 g HFC-134a is charged to the ebulliometer and then HFO-1234 is added in small, measured increments. Temperature depression is observed when HFO-1234 is added to HFC-134a, indicating a binary minimum boiling azeotrope is formed. From greater than about 0 to about 51 weight percent HFO-1234, the boiling point of the composition changed by about 1.3° C. or less. The binary mixtures shown in Table 1 were studied and the boiling point of the compositions changed by less than about 2° C. The compositions exhibit azeotrope and/or azeotrope-like properties over this range.

TABLE 1

HFO-1234/HFC-134a compositions at 14.41 psia

| T. (C) | Wt. % 134a | Wt. % Trans-1234ze |
|---|---|---|
| −25.288 | 100.00 | 0.00 |
| −25.522 | 99.07 | 0.93 |
| −25.581 | 95.01 | 4.99 |
| −25.513 | 91.74 | 8.26 |
| −25.444 | 86.21 | 13.79 |
| −25.366 | 77.87 | 22.13 |
| −24.926 | 67.47 | 32.53 |
| −24.633 | 61.67 | 38.33 |
| −24.291 | 55.23 | 44.77 |
| −23.998 | 51.05 | 48.95 |

Example 2

An ebulliometer consisting of vacuum jacketed tube with a condenser on top which is further equipped with a Quartz Thermometer is used. About 35 g HFC-125 is charged to the ebulliometer and then HFO-1234 is added in small, measured increments. Temperature depression is observed when HFO-1234 is added to HFC-125, indicating a binary minimum boiling azeotrope is formed. From greater than about 0 to about 24 weight percent HFO-1234, the boiling point of the composition changed by about 2° C. or less. The binary mixtures shown in Table 1 were studied and the boiling point of the compositions changed by less than about 6° C. The compositions exhibit azeotrope and/or azeotrope-like properties over this range.

TABLE 2

HFO-1234/HFC-125 compositions at 14.40 psia

| T. (C) | Wt. % 125 | Wt. % Trans-1234ze |
|---|---|---|
| −48.446 | 100.00 | 0.00 |
| −48.546 | 99.42 | 0.58 |
| −48.898 | 96.35 | 3.65 |
| −48.697 | 92.27 | 7.73 |
| −47.842 | 84.68 | 15.32 |
| −46.686 | 77.49 | 22.51 |
| −44.856 | 68.02 | 31.98 |
| −43.177 | 59.57 | 40.43 |
| −42.513 | 56.97 | 43.03 |

Example 3

An ebulliometer consisting of vacuum jacketed tube with a condenser on top which is further equipped with a Quartz Thermometer is used. About 17 g HFC-152a is charged to the ebulliometer and then HFO-1234 is added in small, measured increments. Temperature depression is observed when HFO-1234 is added to HFC-152a, indicating a binary minimum boiling azeotrope is formed. From greater than about 0 to about 30 weight percent HFO-1234, the boiling point of the composition changed by about 0.8° C. or less. The binary mixtures shown in Table 1 were studied and the boiling point of the compositions changed by less than about 1° C. The compositions exhibit azeotrope and/or azeotrope-like properties over this range.

TABLE 3

HFO-1234/HFC-152a compositions at 14.39 psia

| T. (C) | Wt. % 152a | Wt. % Trans-1234 |
|---|---|---|
| −23.455 | 100.00 | 0.00 |
| −23.504 | 99.34 | 0.66 |
| −23.631 | 96.83 | 3.17 |
| −23.778 | 94.99 | 5.01 |
| −23.817 | 87.22 | 12.78 |
| −24.160 | 81.49 | 18.51 |
| −23.797 | 70.59 | 29.41 |

Example 4

An ebulliometer consisting of vacuum jacketed tube with a condenser on top which is further equipped with a Quartz Thermometer is used. About 18 g HFO-1234 is charged to the ebulliometer and then HFC-227ea is added in small, measured increments. Temperature depression is observed when HFC-227ea is added to HFO-1234, indicating a binary minimum boiling azeotrope is formed. From greater than about 0 to about 53 weight percent HFC-227ea, the boiling point of the composition changed by about 0.7° C. or less. The binary mixtures shown in Table 1 were studied and the boiling point of the compositions changed by less than about 1° C. The compositions exhibit azeotrope and/or azeotrope-like properties over this range.

TABLE 4

HFO-1234/HFC-227ea compositions at 14.44 psia

| T. (C) | Wt. % Trans-1234ze | Wt. % 227ea |
|---|---|---|
| −18.124 | 100.00 | 0.00 |
| −18.310 | 98.87 | 1.13 |
| −18.506 | 93.23 | 6.77 |
| −18.653 | 86.62 | 13.38 |
| −18.741 | 76.24 | 23.76 |
| −18.555 | 66.40 | 33.60 |
| −18.359 | 58.18 | 41.82 |
| −18.114 | 52.63 | 47.37 |
| −18.055 | 46.56 | 53.44 |

What is claimed is:
1. An azeotrope-like composition consisting essentially of effective amounts of trans-1,3,3,3-tetrafluoropropene (transHFO-1234ze) and a compound selected from the group consisting of 1,1-difluoroethane ("HFC-152a"), 1,1,1,2,3,3,3-heptafluoropropane ("HFC-227ea"), 1,1,1,2- tetrafluoroethane ("HFC-134a"), 1,1,1,2,2-pentafluoroethane ("HFC-125") and combinations of two or more of these.

2. A composition comprising an azeotrope-like mixture consisting of transHFO-1234ze and a component selected from the group consisting of 1,1-difluoroethane ("HFC-152a"), 1,1,1,2,3,3,3-heptafluoropropane ("HFC-227ea"), 1,1,1,2-tetrafluoroethane ("HFC-134a"), and 1,1,1,2,2-pentafluoroethane ("HFC-125").

3. An azeotrope-like composition in accordance with claim 1 having a boiling point of from about —26° C. to about —23° C. at a pressure of about 14.4 psia.

4. The azeotrope-like composition of claim 1 which consists essentially of from greater than zero to about 75 weight percent transHFO-1234ze and from about 25 to less than 100 weight percent of HFC-152a.

5. The azeotrope-like composition of claim 1 which consists essentially of from greater than zero to about 50 weight percent transHFO-1234ze and from about 50 to less than 100 weight percent of HFC-152a.

6. The azeotrope-like composition of claim 1 which consists of from about 15 to about 30 weight percent transHFO-1234ze and from about 70 to about 85 weight percent of HFC-152a.

7. An azeotrope-like composition in accordance with claim 6 having a boiling point of from about —26° C. to about —23° C. at a pressure of about 14.4 psia.

8. A sprayable composition comprising a material to be sprayed and a propellant comprising an azeotrope-like composition of claim 1.

9. A refrigerant composition comprising an azeotrope-like composition of claim 1.

10. A refrigeration system comprising a refrigerant of claim 9.

11. A method for cooling an article which comprises condensing a refrigerant composition of claim 9 and thereafter evaporating said refrigerant composition in the vicinity of the article to be cooled.

12. A method for heating an article which comprises condensing a refrigerant composition of claim 9 in the vicinity of the article to be heated and thereafter evaporating said refrigerant composition.

13. A method of recharging a refrigerant system that contains a refrigerant to be replaced and a lubricant comprising the steps of: (a) removing the refrigerant to be replaced from the refrigeration system while retaining a substantial portion of the lubricant in said system; and (b) introducing to the system a refrigerant composition of claim 1.

14. A blowing agent comprising an azeotrope-like composition of claim 1.

15. An azeotrope-like composition comprising effective amounts of trans-1,3,3,3-tetrafluoropropene (transHFO-1234ze) and a compound selected from the group consisting of 1,1,1,2,3,3,3-heptafluoropropane ("HFC-227ea"), 1,1,1,2,-tetrafluoroethane ("HFC-134a"), 1,1,1,2,2-pentafluoroethane ("HFC-125") and combinations of two or more of these.

16. The azeotrope-like composition of claim 15 which consists essentially of from greater than zero to about 75 weight percent transHFO-1234ze and from about 25 to less than 100 weight percent of HFC-134a.

17. The azeotrope-like composition of claim 15 which consists essentially of from greater than zero to about 60 weight percent transHFO-1234ze and from about 40 to less than 100 weight percent of HFC-134a.

18. The azeotrope-like composition of claim 15 which consists essentially of from about 1 to about 40 weight percent transHFO-1234ze and from about 60 to about 99 weight percent of HFC-134a.

19. The azeotrope-like composition of claim 15 which consists essentially of from about 5 to about 35 weight percent transHFO-1234ze and from about 65 to about 95 weight percent of HFC-134a.

20. An azeotrope-like composition in accordance with claim 19 having a boiling point of from about –26° C. to about –23° C. at a pressure of about 14.4 psia.

21. The azeotrope-like composition of claim 15 which consists essentially of from greater than zero to about 75 weight percent transHFO-1234ze and from about 25 to less than 100 weight percent of HFC-125.

22. The azeotrope-like composition of claim 15 which consists essentially of from greater than zero to about 60 weight percent transHFO-1234ze and from about 40 to less than 100 weight percent of HFC-125.

23. The azeotrope-like composition of claim 15 which consists essentially of from about 1 to about 40 weight percent transHFO-1234ze and from about 60 to about 99 weight percent of HFC-125.

24. The azeotrope-like composition of claim 15 which consists essentially of from about 2 to about 15 weight percent transHFO-1234ze and from about 85 to about 98 weight percent of HFC-125.

25. An azeotrope-like composition in accordance with claim 24 having a boiling point of from about –49° C. to about –42° C. at a pressure of about 14.4 psia.

26. The azeotrope-like composition of claim 15 which consists essentially of from greater than zero to about 75 weight percent HFC-227ea and from about 25 to less than 100 weight percent of transHFO-1234ze.

27. The azeotrope-like composition of claim 15 which consists essentially of from greater than zero to about 50 weight percent HFC-227ea and from about 50 to less than 100 weight percent of transHFO-1234ze.

28. The azeotrope-like composition of claim 15 which consists essentially of from about 5 to about 35 weight percent HFC-227ea and from about 65 to about 95 weight percent of transHFO-1234ze.

29. An azeotrope-like composition in accordance with claim 28 having a boiling point of from about –17° C. to about –19° C. at a pressure of about 14.4 psia.

30. A sprayable composition according to claim 8 wherein the sprayable composition is an aerosol.

31. A sprayable composition according to claim 8 Further comprising a drug or a biologically active material.

32. A sprayable composition according to claim 31 wherein said drug or a biologically active material is selected from anti-asthma and anti-halitosis medications.

* * * * *